(12) United States Patent
Hornung et al.

(10) Patent No.: US 8,016,806 B2
(45) Date of Patent: Sep. 13, 2011

(54) INCONTINENCE ARTICLE IN THE FORM OF PANTS

(75) Inventors: Fridmann Hornung, Sanhago (CL);
Wolfgang Ostertag, Gerstetten (DE);
Benjamin Wenzel, Heidenheim (DE)

(73) Assignee: Paul Hartmann Aktiengesellschaft,
Heidenheim (DE)

( * ) Notice: Subject to any disclaimer, the term of this patent is extended or adjusted under 35 U.S.C. 154(b) by 338 days.

(21) Appl. No.: 12/292,299

(22) Filed: Nov. 17, 2008

(65) Prior Publication Data

US 2009/0143756 A1     Jun. 4, 2009

(30) Foreign Application Priority Data

Nov. 21, 2007 (DE) .......................... 10 2007 056 126

(51) Int. Cl.
*A61F 13/15* (2006.01)
(52) U.S. Cl. ............ 604/385.3; 604/385.22; 604/385.23; 604/385.26; 604/385.24; 604/385.27; 604/385.29; 604/385.28
(58) Field of Classification Search ............ 604/385.22, 604/385.23, 385.24, 385.26, 385.27, 385.28, 604/385.29, 385.3
See application file for complete search history.

(56) References Cited

U.S. PATENT DOCUMENTS

| | | | |
|---|---|---|---|
| 5,940,887 A | 8/1999 | Rajala | |
| 6,497,696 B1 | 12/2002 | Freiburger | |
| 6,808,582 B2 * | 10/2004 | Popp et al. ................. | 156/229 |
| 2002/0049421 A1 | 4/2002 | Hayase | |
| 2003/0028166 A1 | 2/2003 | Price | |
| 2003/0088230 A1 | 5/2003 | Balogh | |
| 2004/0122412 A1 | 6/2004 | Morman | |
| 2005/0148965 A1 | 7/2005 | Richlen | |
| 2006/0173436 A1 | 8/2006 | Krautkramer | |

FOREIGN PATENT DOCUMENTS

| | | |
|---|---|---|
| DE | 10 2004 032 377 | 1/2006 |
| EP | 1 214 032 | 6/2002 |
| EP | 1 384 459 | 1/2004 |
| EP | 1 844 748 | 10/2007 |
| JP | 11 036103 | 2/1999 |
| JP | 2000 014700 | 1/2000 |
| JP | 2003 126148 | 5/2003 |
| WO | WO 2004/052260 | 6/2004 |

* cited by examiner

*Primary Examiner* — Jacqueline F Stephens
(74) *Attorney, Agent, or Firm* — Paul Vincent

(57) ABSTRACT

An incontinence article comprising front and back belly sections connected at side seams forming belly and back bands, continuous in the hip direction having a hip opening closed in the hip direction, and a crotch section comprising an absorbent body, extending longitudinally between and permanently attached to the belly and back sections, wherein the crotch, belly, and back sections define leg openings, the belly and back sections have an edge contour extending towards a transverse center axis, wherein first elastification means in the belly and back sections extend parallel to each other in the hip direction and wherein, in the belly and back sections, second elastification means extend from two side seam areas towards a longitudinal center axis of the article in a curved shape, thereby fanning out with increasing separation from each other, where the second elastification means fan out, the restoring force from extensive stretching of this area is smaller than that from extensive stretching of an area on the hip side, having only the first elastification means.

27 Claims, 5 Drawing Sheets

INCONTINENCE ARTICLE IN THE FORM OF PANTS

BACKGROUND OF THE INVENTION

The invention concerns an incontinence article in the form of pants for receiving body excrements, comprising a front belly section and a rear back section, which are connected to each other at side seam areas on both sides during production to form a belly and back band, which is continuous in the transverse or peripheral hip direction and has a hip opening that is closed in the peripheral hip direction, and a crotch section which has an absorbent body and extends in a longitudinal direction between the belly section and the back section, and is permanently attached to the belly section and to the back section, wherein the crotch section as well as the belly section and the back section define the leg openings of the incontinence article. A three-component incontinence article of this type is disclosed e.g. in WO 2004/052260 A1. In this specific product concept, an H-shaped basic structure of the incontinence article is realized by joining the crotch section, which extends in the longitudinal direction, to the belly section, which extends substantially in the transverse or peripheral hip direction, and to the correspondingly extending back section when these three components are flatly extended. The incontinence article is then modularly designed from the components crotch section, belly section and back section. These components are advantageously initially connected to each other via the crotch section, and preferably after that, the side seam areas of the belly section are connected to those of the back section on both sides. This connection is realized by the manufacturer to obtain the shape of pants. This connection is typically permanent. However, it may also be provided that the pants can be opened, in particular, along a breaking line which may extend, in particular, in the side seam area, e.g. for removing a used incontinence article from a person who is in need of care.

Incontinence articles in the form of pants differ, in principle, from incontinence articles of normal diaper shape that can be opened and closed in that the hip size is generally predetermined and the article can be adjusted to different body sizes by providing a number of different basic sizes that can be elastically stretched. Towards this end, elastification means, in particular, in the form of bands or threads, often called Lycra threads, are generally connected in a prestrained state (stretch-bond method) to chassis materials of the incontinence article, i.e. they are fixed in the prestrained state to the chassis materials e.g. by means of glue. Due to their pretension, these elastification means gather the chassis materials to thereby form crimps. The incontinence article or the elasticised chassis materials of the incontinence article can be elastically stretched again when the incontinence article is applied to the user like pants. Several incontinence articles in the form of pants comprising elasticised chassis materials of this type have been disclosed and are discussed e.g. also in the above-mentioned document WO 2004/052260 A1.

For producing the H-shaped basic structure, i.e. for connecting the crotch section to the belly section and the back section, these components must be joined in such a fashion that all requirements for appropriate use are met in order to prevent the connection between the crotch section and the belly section or back section from being detached under great tensile stress. Large forces may be generated during wear of an incontinence article in the form of pants, e.g. due to the weight of an absorbent element that is loaded with a considerable amount of fluid. Large tensile forces are moreover transferred within the chassis materials by the elastification means that are usually joined to the chassis materials using a stretch-bond method, and also by tensile forces that are transferred by movement of the user. It has thereby turned out that this high tensile stress surprisingly occurs both with mobile users who use the incontinence article substantially as a piece of underwear, and also with bedridden persons who are in need of care and can move only to a very limited degree. The chassis materials of the incontinence article cannot compensate for the tensile stress due to sudden and, in particular, also slow movements. In situations like this, the joining connections of the incontinence article are heavily strained, i.e. in particular between the crotch section and the belly section and between the crotch section and the back section.

If a large amount of, in particular, extensively applied adhesive material is used to produce a stable and permanent tension-proof connection between the crotch section and the belly section and between the crotch section and the back section, the overlapping area between the crotch section and the belly section or back section is disadvantageously stiffened. This is perceived as being unpleasant and can also impair the desired stretchability of the chassis materials in this area, wherein it must be noted at this point that an extensive stretchability is often not desired in this area. It is thereby also problematic that adhesive materials impede the desired product properties.

Departing therefrom, it is the object of the present invention to solve the above-mentioned problems, i.e. provide a stable connection between the crotch section and the belly section and between the crotch section and the back section of an incontinence article in the form of pants of this type without impairing the wear comfort or having other negative effects on the functionality of the incontinence article.

SUMMARY OF THE INVENTION

This object is achieved in accordance with the invention by an incontinence article comprising the features of the independent claim.

Since both the belly section and the back section have an edge contour that extends towards the transverse center axis to define the leg openings, a large extensive overlap between the crotch section and the belly section, and the crotch section and the back section can be obtained, which is essential for forming a stable connection between the three components of the incontinence article. This also provides a contour line that corresponds to the leg openings. Moreover, an area of the belly section and of the back section is provided on the crotch side facing the leg openings, which extends towards the transverse center axis and into which the second elastification means can be introduced in a specific fashion in correspondence with the stress conditions that are desired at that location.

The first elastification means, which extend at a separation from each other and parallel to each other in the transverse or peripheral hip direction, are provided for extensive elastification of the belly section and the back section. They preferably have the same pretension and are substantially used to extensively elasticise the belly section and the back section in a continuous and even fashion in the area distinctly above the leg openings. It is, however, possible that the first elastification means have a greater pretension in an upper hip edge area, or that several of these elastification means are disposed at a smaller distance from each other in order to realize a somewhat stronger elastification on the hip edge.

Since the crotch section has a very large maximum width in the transverse direction of at least 200 mm and the backsheet material and/or topsheet material project on both sides of the absorbent body, i.e. on the left-hand and right-hand side added together, by at least 25% with respect to the maximum width of the crotch section, a large overlapping area between the crotch section and the belly section and also between the crotch section and the back section is realized. The chassis materials of the crotch section largely project in the transverse direction past the absorbent body, thereby realizing a large-surface overlapping area between the crotch section and the belly section or back section outside of the absorbent body which, in turn, is technically advantageous with respect to function. The connection between the crotch section and the belly section or back section must be optimized, thereby minimally influencing the components of the absorbent body. The larger the overlapping area between the crotch section and the belly section or the crotch section and the back section outside of the absorbent body, the larger the degrees of freedom with respect to formation of a fully functional connection. When the chassis materials largely project in the transverse direction past the absorbent body, additional leg elastification means can advantageously be provided in the longitudinal direction on both sides of the absorbent body, which extend at a maximum separation from the absorbent body. In accordance with the invention, this prevents the leg elastification means from exerting forces that would distort the absorbent body, i.e. subject it to tension and pressure. Such unpredictable forces have a negative effect on the absorption behavior of the absorbent body with the result of uncontrolled densification or widening of absorbent body areas, which negatively affects the intended absorption behavior. In this connection, the relatively large overlapping area between the crotch section and the belly section or between the crotch section and the back section is also characterized by the surface fraction of the crotch section with respect to the overall surface of the incontinence article of 25 to 55% and moreover, in that the crotch section overlaps at least 12% of the surface of the belly section and at least 20% of the surface of the back section. In total, the features of the independent claim provide an incontinence article in the form of pants having the above-mentioned three-component structure, which realizes a reliable connection between the components without thereby impairing the wear comfort or the functionality of the incontinence article, or its components.

In a further development of the invention, the surface fraction of the crotch section with respect to the overall surface of the incontinence article is advantageously 30 to 47%, in particular 35 to 47% and moreover in particular 35 to 45%.

It has moreover turned out to be advantageous when the sum of the overlap of the back sheet material and/or the top sheet material in the transverse direction past the absorption body on both sides thereof, i.e. on the left-hand and right-hand side added together, amounts to at least 25%, in particular 30 to 45%, moreover in particular 35 to 45%, with respect to the maximum width of the crotch section (i.e. with respect to the maximum extension of the crotch section in the transverse direction).

In a further development of the invention, the overlap region between the crotch section and the belly section is configured in such a manner that the crotch section overlaps 15 to 40%, in particular 15 to 35%, and moreover, in particular 15 to 25%, of the surface of the belly section. The crotch section advantageously overlaps the belly section with a surface of 25,000 to 45,000 mm$^2$.

In a further development of the invention, the overlap region between the crotch section and the back section is configured in such a manner that the crotch section overlaps 20 to 40%, in particular 20 to 35%, and moreover, in particular 22 to 32%, of the surface of the back sections. The crotch section advantageously overlaps the back section with a surface of 35,000 to 65,000 mm$^2$, in particular 40,000 to 55,000 mm$^2$.

The overlap between the crotch section and the back section is moreover advantageously larger than the overlap between the crotch section with the belly section.

Moreover, in a particularly advantageous fashion, the crotch section can be connected to the belly section and/or the back section without applying adhesive to the entire surface. It has turned out that the properties of the chassis materials are less influenced when the adhesive is not provided on the entire surface compared to when the adhesive is applied to the entire surface for forming the connection between the crotch section and the belly section or the crotch section and the back section. When the adhesive is not applied to the entire surface, it may be applied e.g. in a striped pattern, a web-shaped continuous or non-continuous grid structure, island-shaped areas or a striped adhesive structure.

The incontinence article in accordance with the invention can be advantageously structured such that the absorbent body also overlaps 5 to 20%, in particular 5 to 15%, of the surface of the belly section and/or 10 to 20%, in particular 10 to 15%, of the surface of the back section.

The extension of the belly section and the back section in the side seam area in the longitudinal direction is preferably at least 100 mm, in particular at least 150 mm, and in particular 150 to 220 mm.

The minimum separation between the belly section and the back section in the longitudinal direction is preferably 250 to 400 mm.

The maximum extension of the crotch section in the transverse direction is advantageously 200 to 350 mm, in particular 250 to 320 mm.

The relatively large projection of the backsheet material and/or the topsheet material past both sides of the absorbent body produces a wide crotch section with a relatively narrow absorbent body. It is thereby possible to provide leg elastification means in the crotch section, which extend along the leg openings and have a relatively large separation from the absorbent body that comprises a good deal of material and is therefore rigid. As a result thereof, the leg opening edges of the crotch section on both sides can be easily sealed and adjusted. In this case, the absorbent body that has a good deal of material and is torsionally rigid compared to the thin chassis materials facilitates formation of a liquid-tight leg termination. For this reason, a liquid-tight leg termination can be obtained without extremely high tension which has, in turn, a positive effect on the wear comfort of the incontinence article.

In a further particularly advantageous design of the invention, the leg elastification means terminate in the longitudinal direction at least 10 mm, in particular at least 20 mm upstream of the second elastification means. The leg elastification means preferentially terminate in the longitudinal direction upstream of the belly section and/or the back section. The tension and restoring force exerted by them therefore does not influence the inventive tension ratios within the area of the belly section and the back section on the crotch side facing the leg openings, where the fanning-out second elastification means are provided.

The leg elastification means moreover preferentially extend at a variable separation from the absorbent body and have a larger separation from the absorbent body at their longitudinal ends than in the center.

Thread-shaped or band-shaped elastification means, such as rubber or polyether polyurethane or polyester polyurethane threads, preferably elastic threads such as Lycra® or Spandex® threads, are preferably used as leg elastification means. The leg elastification means preferably have a thickness of 300 to 1500 dtex, in particular, 500 to 1200 dtex, moreover, in particular 500 to 900 dtex.

The leg elastification means are preferably fixed with a pretension of 1.5 to 6.0, in particular 2.5 to 4.5, to the chassis-forming cover materials of the crotch section. The pretension is defined as the ratio of the extended state to the non-stretched/relaxed state of the elastification means.

The development of incontinence articles in the form of pants showed that a maximum area of the incontinence article should be elastically flexible, i.e. be stretchable in accordance with the body shape of the user. One therefore assumed that a maximum part of the cover-forming chassis materials of the incontinence article should be provided with elastically stretchable or elasticised materials, in particular, by introducing the above-mentioned elastification means in the stretch-bond method, which assumption is not always correct. Irrespective thereof or in addition thereto, one tried to elasticise the leg openings of the incontinence article, if possible, in a continuous fashion in order to obtain reliable side leakage protection. However, one did not recognize that elastification of chassis materials, in particular, by introducing linearly extending elastification means, also entails considerable disadvantages. An extensive, i.e. substantially continuously extending elastification of chassis materials makes the pants-shaped incontinence article, to a certain degree, generally adaptable to different body shapes, i.e. the article can be at least properly positioned on the user. This often generates very large tensile stress in the chassis materials, which has a negative effect on the user. The elastification means thereby often cut into the skin surface of the user, which is perceived as unpleasant and can cause pain, skin irritations and, in particular, in a humid climate, even skin injuries. Highly strained chassis materials often tightly abut the skin surface of the user, which, even when breathable materials are used, produces a humid micro climate in the region of the skin surface, which can also have severe consequences for the skin surface of the user. In this case, instead of a gas phase, a liquid phase forms directly next to the skin surface. Irrespective thereof, great pretension in the area of the elastification means produces a great amount of frills, i.e. a large number of folds or crimps per centimeter (as viewed in the direction of the elastic action of the elastification means). This three-dimensional wavy structure is then pressed against the skin surface with great strain exerted by the elastification means, and causes relative motions, in particular, when the user is highly mobile, which again irritate the skin surface and cause unpleasant or even medically problematic skin irritations.

Whenever elastification means are guided in a curved shape or transverse direction with respect to a machine direction, which is often done to obtain an extensive elastification substantially of the overall chassis material, there is the problem that, due to the component transverse to the machine direction, a larger path must be covered, thereby increasing the pretension of the elastification means in the course of the stretch-bond method. This typically results in a stronger elastic strain resistance of the corresponding chassis areas compared to areas where the elastification means are introduced extending in the machine direction, which could, in turn, cause severe problems.

The first elastification means, which extend at a separation from each other and parallel to each other in the transverse or peripheral hip direction, are provided for extensive elastification of the belly section and the back section. They preferably have the same pretension and are substantially used to extensively elasticise the belly section and the back section in a continuous and even fashion in the area distinctly above the leg openings. It is, however, possible that the first elastification means have a greater pretension in an upper hip edge area, or that several of these elastification means are disposed at a smaller distance from each other in order to realize a somewhat stronger elastification on the hip edge.

The present invention also showed i.a. that the stress conditions in the above-mentioned area of the belly section and the back section on the crotch side facing the leg openings cause the above-mentioned problems and can be designed in such a fashion that the above-mentioned problems are eliminated or reduced. In accordance with the invention, the area on the crotch side facing the leg openings, in which the second elastification means fan out towards the longitudinal center axis, is designed in such a fashion that the restoring force that is generated when this area is extensively stretched, is smaller compared to extensive stretching in an area on the hip side where only the first elastification means are provided. "Area on the hip side" means that this area is located in the longitudinal direction outside of the area on the crotch side that faces the leg openings and comprises the fanning-out second elastification means. The restoring force is that force that is exerted by the belly section and the back section in response to extensive stretching in the direction of extension of the elastification means. In accordance with the invention, it has turned out to be important for the area on the crotch side facing the leg openings to have a smaller restoring force in case of extensive stretching along the second elastification means than areas located next to it in the longitudinal direction, which are further away from the crotch area and the leg openings, in particular, those areas where the first elastification means are disposed. This improves the wear comfort of the incontinence article, and the above-described problems are reduced, since the incontinence article can be stretched to a larger extent in the crotch area or in the area of the leg openings in accordance with the body shape without directly increasing the restoring forces, which would entail the above-described unpleasant consequences.

In order to determine the restoring forces, the areas of the chassis to be measured can be fixedly clamped directly and quasi non-destructively between two clamping jaws of defined identical clamping jaw width, and the restoring forces can be determined under a defined extension, which simulates the state of wear, of the areas to be measured by, in particular, 30% or 50% or 80% of the initial length (of the clamping jaw separation during fixing of the area to be measured in the non-stretched state). The clamping jaws should fix as many as possible, however, at least two adjacent elastification means of the area to be measured, and be substantially oriented perpendicularly to the extension of the elastification means, such that the clamps are extended substantially in the direction of extension of the elastification means.

In a further design of the present invention, it has turned out that the tension ratios in the above-mentioned area of the belly section and the back section on the crotch side facing the leg openings are essential with respect to the wear comfort and can be designed to improve the wear comfort. Towards this end, the area on the crotch side facing the leg openings, where the second elastification means fan out towards the longitudinal center axis, is designed such that, when this area is extensively stretched, the resulting restoring force decreases towards this crotch section.

Considering this area of the belly section and the back section on the crotch side facing the leg openings in a direction starting from the respective side seam area towards the crotch section, i.e. towards a longitudinal center axis of the incontinence article and substantially towards the curved fanning-out of the second elastification means, the restoring force generated by extensive stretching is reduced in this direction. This is the force that is exerted by the belly section and the back section in response to extensive stretching. A reduction of this restoring force, which is naturally transferred to the user, considerably improves the wear comfort of the incontinence article.

It is also particularly advantageous to reduce the restoring force in the above-mentioned area of the belly section and the back section on the crotch-side facing the leg openings in such a fashion that a decreasing number of folds is formed per cm in the transverse direction of the incontinence article in the direction towards the crotch section. In this case, the belly section and the back section can be stretched in correspondence with the body shape of the user, thereby preventing that the resulting elastic forces gather the chassis material and form a plurality of folds. As mentioned above, a reduction of restoring forces in the direction towards the crotch area means that the force that is generated due to extensive stretching decreases with decreasing separation from the crotch section. The restoring force due to extensive stretching is thereby larger in an area closer to the side seam than in an area closer to the crotch section.

The above-mentioned stress conditions can be obtained in the most different ways, e.g. by using materials, which have different elasticities in the transverse direction, for the area on the crotch side facing the leg openings, where the second elastification means are also provided. It is also feasible to reduce the pretension of the second elastification means with decreasing separation from the crotch section, i.e. from the outside to the inside towards a longitudinal center axis. Moreover, it is also feasible to reduce the restoring force under extensive stretching by increasing the distance between the second elastification means, wherein one must take care that this is not cancelled by a strong increase in pretension due to the fan-shaped extension of the elastification means or is even over-compensated by an increasing restoring force.

It has turned out to be particularly advantageous for a minimum separation between the second elastification means (separation between directly neighboring elastification means) in the side seam areas to be 3 to 8 mm, in particular 3 to 7 mm, and moreover in particular 3 to 6 mm.

It has also turned out to be advantageous for a maximum separation between the second elastification means (separation of directly neighboring elastification means) on an absorbent body edge or on a longitudinal edge of the crotch section to be 7 to 35 mm, in particular 10 to 32 mm and moreover, in particular, 12 to 30 mm.

It has also turned out to be advantageous for the second elastification means to have a fanning-out degree F.

$$F=(A-B)/B*100\%$$

of 50 to 900%, in particular 100 to 700%, and moreover, in particular 150 to 550%.

The fanning-out degree F. is thereby defined as the ratio between the separation increase (A−B) and the minimum separation (B) in percent. The values A and B are thereby defined as the separation between the outermost second elastification means in the longitudinal direction and the innermost second elastification means in the longitudinal direction (i.e. not the separation between directly neighboring second elastification means), i.a. A as the maximum separation, in particular, on the longitudinal edge of the crotch section or on the absorbent body edge, and B as the minimum separation, in particular, in the side seam area. It was also found out that the fanning-out degree F. of the second elastification means is advantageously larger in the back section than in the belly section.

The above-mentioned problems are typically more severe with respect to the back or bottom area due to the natural body shape of the back or belly region of a user. For this reason, the maximum separation between the second elastification means on an absorbent body edge in the back section is advantageously larger than in the belly section.

It is quite feasible for the second elastification means to extend in a continuous fashion from one side seam area to the other side seam area, which simplifies, in particular, introduction in a continuous production method compared to a "cut-and-place" process. Since the crotch section overlaps the belly section and the back section, the absorbent body, which comprises a good deal of material, and the belly section and/or the back section typically also overlap or cover each other, and thereby also the area of the belly section and the back section on the crotch side facing the leg openings, in which the second elastification means extend. The absorbent body, which comprises a good deal of material, thereby usually impairs the elastic stretchability of the chassis materials. It is moreover not necessarily advantageous to additionally strain the absorbent body which comprises a good deal of material. For this reason, it may be advantageous to deactivate the elastic properties of the second elastification means in an overlapping area with the absorbent body of the crotch section. This deactivation may e.g. be realized by a number of separating cuts through the second elastification means in the overlapping area with the absorbent body, wherein other separating methods are also feasible, e.g. using ultrasound welding or laser.

It must be mentioned that the elastic properties of the first elastification means may also be deactivated in the overlapping area with the absorbent body.

It has been mentioned above, that, irrespective of the stress conditions to be produced in accordance with the invention, the second elastification means may be exposed to greater elongation and thereby to a higher pretension during production of the incontinence article in correspondence with their fanned-out extension than in an area which is not fanned out and in which they substantially extend at equal distances from each other and in the machine direction. This stronger pretension may typically result from introduction of the second elastification means in a conventional stretch-bond method which is therefore not described in detail.

With respect to the overall dimensions of the incontinence article, it is advantageous for the separation (C) between the innermost second elastification means of the belly section facing the crotch area and the corresponding innermost second elastification means of the back section facing the crotch area to be 250 to 420 mm.

The separation between the innermost second elastification means facing the crotch area and the edge contour, delimiting the leg openings, of the area of the belly section and the back section on the crotch side facing the leg openings is preferably 2 to 40 mm, moreover preferably 3 to 30 mm, in particular preferably 4 to 15 mm.

Thread-shaped or band-shaped elastification means, such as rubber or polyetherpolyurethane or polyesterpolyurethane threads, preferably elastic threads such as Lycra® or Spandex® threads are used as the first and/or second elastification means. The first and/or second elastification means preferably have a strength of 300 to 1500 dtex, in particular 500 to 900 dtex, moreover in particular 500 to 600 dtex.

The first and/or second elastification means are preferably fixed with a pretension of 1.5 to 6.0, in particular 2.5 to 5.0, to the chassis-forming cover materials of the belly section and the back section (stretch-bonding method). The pretension is thereby defined as the factor of the degree of extension compared to the non-stretched/relaxed state of the elastification means.

It has turned out to be advantageous for the belly section and the back section to be substantially continuously, extensively transversely elasticised in the longitudinal direction at least outside of the absorbent body, wherein in this case, the inventive stress conditions must also be maintained or realized.

The chassis-forming materials of the belly section and/or the back section preferably comprise non-woven materials, such as spunbonded non-woven materials, card webs or Through Air bonded card webs. With particular preference, the chassis-forming material of the belly section and/or the back section comprises a spunbonded non-woven material. The non-woven materials that are used for the belly section and/or the back section advantageously have a surface density of 10 to 30 $g/m^2$, moreover preferably 15 to 25 $g/m^2$. With particular preference, the belly section and the back section have a spunbonded non-woven material of polypropylene, in particular, with a surface density of 15 to 25 $g/m^2$.

The crotch section advantageously comprises a liquid-impermeable backsheet material and a non-woven topsheet material. The backsheet comprises, in particular, a foil, in particular, of a surface density of 18 to 40 $g/m^2$. The backsheet comprises, in particular, a foil which is liquid-tight but at the same time breathable during use, i.e. a water vapor-permeable, in particular, micro porous foil. The water vapor permeability of the backsheet is, in particular, at least 300 $g/m^2/24$ h, moreover, in particular at least 1000 $g/m^2/24$ h, moreover, in particular at least 2000 $g/m^2/24$ h, moreover, in particular at least 3000 $g/m^2/24$ h, moreover, in particular at least 4000 $g/m^2/24$ h, moreover, in particular at most 6000 $g/m^2/24$ h measured according to DIN 53 122-1 (Edition: 2001-08).

The absorbent body comprises materials that absorb body liquids, such as natural and synthetic fibers, in particular, cellulose fibers, preferably in the form of cellulose fluff. The absorbent body moreover preferably comprises super-absorbent materials (SAP), in particular, on the basis of surface-cross-linked, partially neutralized polyacrylates.

The crotch section or the longitudinal edges of the crotch section, which define the leg openings, advantageously have a curved contour.

Further features, details and advantages of the invention can be extracted from the enclosed claims, the drawing and the following description of a preferred embodiment of the inventive incontinence article. In the drawing:

DESCRIPTION OF THE PREFERRED EMBODIMENT

Figure 6:
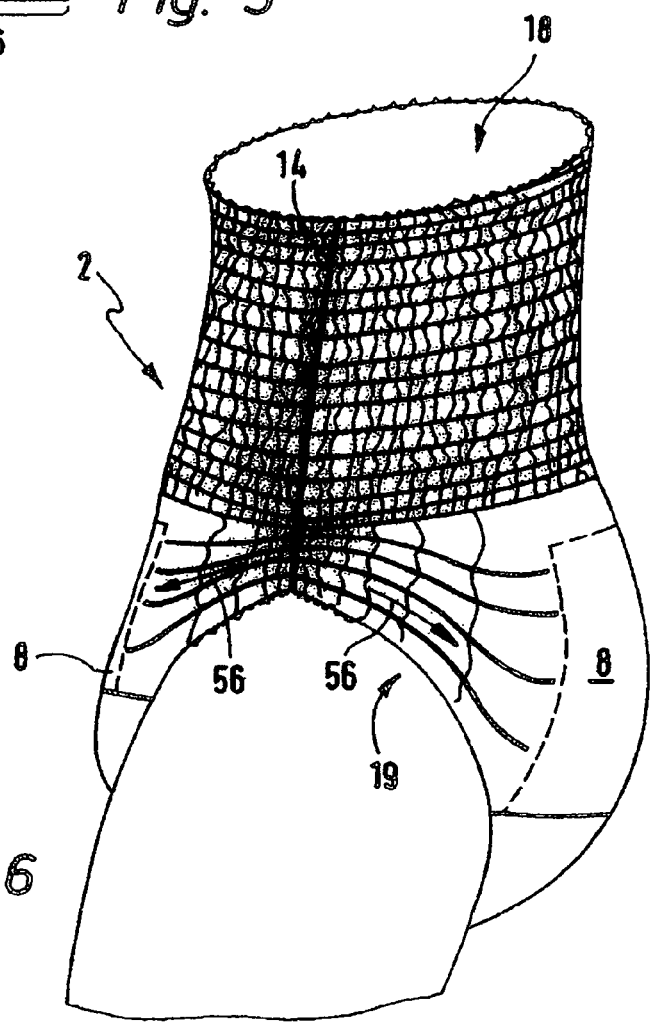
FIG. 6 shows a perspective view (schematic) of the incontinence article according to FIG. 1, which is applied to a user.

The figures show an incontinence article in the form of pants, which is designated in total by reference numeral 2, for receiving solid and liquid body excrements. The incontinence article 2 is formed from three components which can be largely independently produced, i.e. a front belly section 4, a rear back section 6, and a crotch section 8 which is disposed therebetween and comprises an absorbent body 7, wherein the crotch section 8 overlaps a substantial surface portion of the belly section 4 and also of the back section 6, and is permanently connected in the overlapping area during production. As can be gathered from FIG. 1, this yields an H-shaped basic structure of the incontinence article with a longitudinal direction 9. The joined components (FIG. 1) are then also connected to each other at the respective lateral longitudinal edge sections 10, 12 of the belly section 4 and the back section 6 during production in order to form the pants shape (schematically shown in FIG. 6), thereby forming side seam areas 14 on both sides (FIG. 6). In this pants-shaped state of the incontinence article, which is realized by the manufacturer, the belly section 4 and the back section 6 continuously extend in the transverse or peripheral hip direction 16 to the side seam areas 14 and thereby define a hip opening 18, which is closed in the peripheral hip direction, and leg openings 19 through which the user applies the incontinence article like a pair of pants.

The belly section 4 can be divided into an area 20 on the hip side and an area 22 on the crotch side facing the leg openings. A corresponding subdivision is provided in the back section 6, i.e. also into an area 24 on the hip side and an area 26 on the crotch side facing the leg openings.

First elastification means 28 are provided in the area 20 of the belly section 4 on the hip side and in the area 24 of the back section 6 on the hip side, which may be, in particular, thread-like elastification means, such as Lycra threads, which are pretensioned and connected to the sheet materials (chassis materials) of the belly section 4 and the back section 6 in a so-called stretch-bond method. These first elastification means 28 extend in the transverse or peripheral hip direction 16 from one side seam area 14 to the other.

The section 22 of the belly section 4 or 26 of the back section 6 on the crotch side facing the leg openings 19 has an edge contour 32 or 34 which extends towards a transverse center axis 30 of the crotch section 8 and differs from the transverse or peripheral hip direction 16. This edge contour 32, 34 is also curved in the representation of FIG. 1 and therefore suited for delimiting the leg openings 19. The shape of the area 22 or 26 on the crotch side facing the leg openings also realizes a relatively large overlapping area 36, 38 between the crotch section 8 and the belly section 4 or back section 6, which is essential in view of a tear-resistant connection between the crotch section 8 and the belly section 4 or back section 6. The larger the overlapping area 36, 38, the smaller the amount of glue required with respect to the surface of the overlapping area, which is advantageous with respect to the rigidity of the chassis materials. The components can be connected without having to provide glue on the entire surface.

Figure 1:
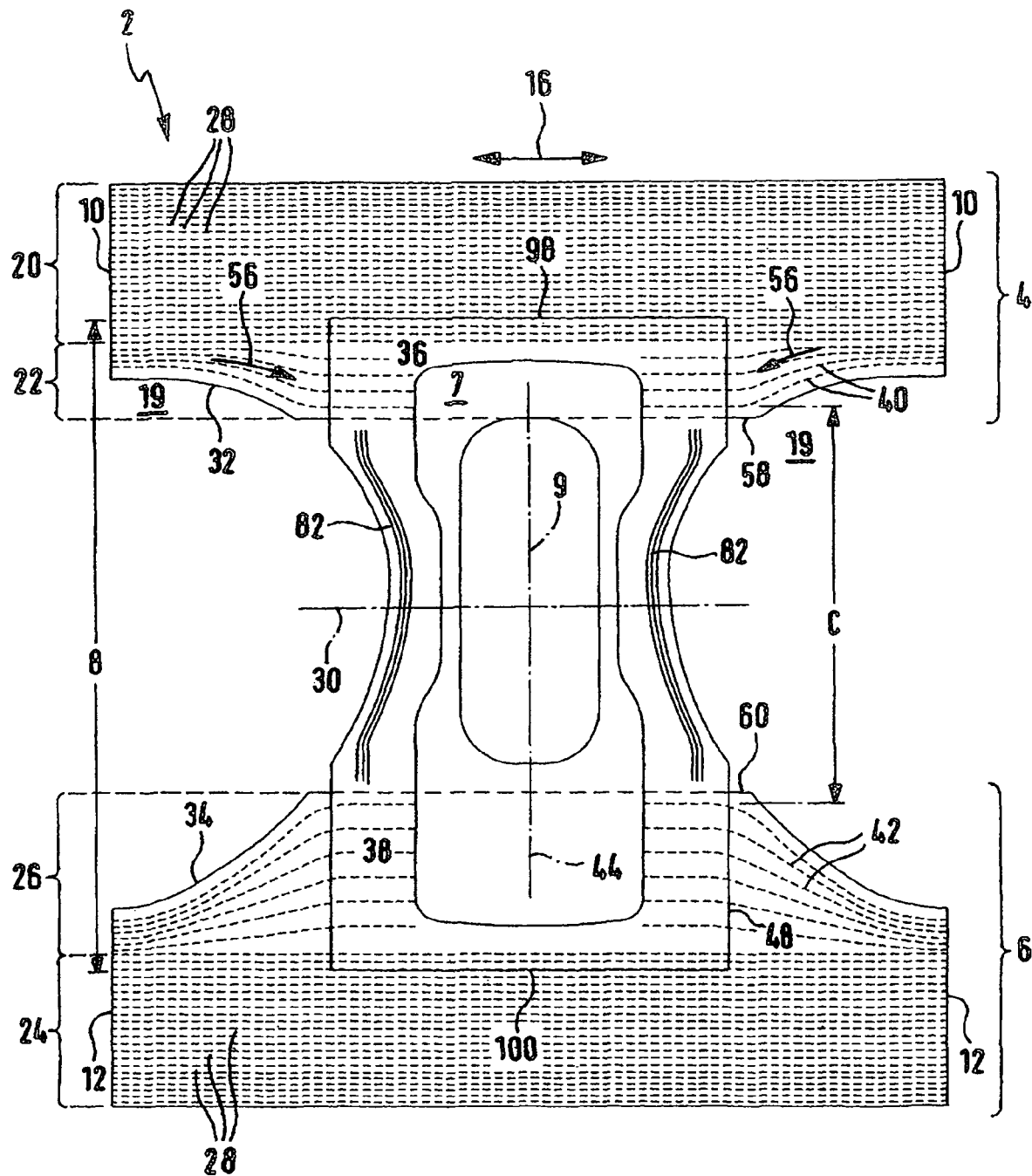
FIG. 1 shows a top view of an inventive incontinence article, which shows a belly section, a back section and a crotch section that connects them, of the incontinence article, which are not yet connected to form a pants shape, but are illustrated in a flat and extended state.
Figure 2:
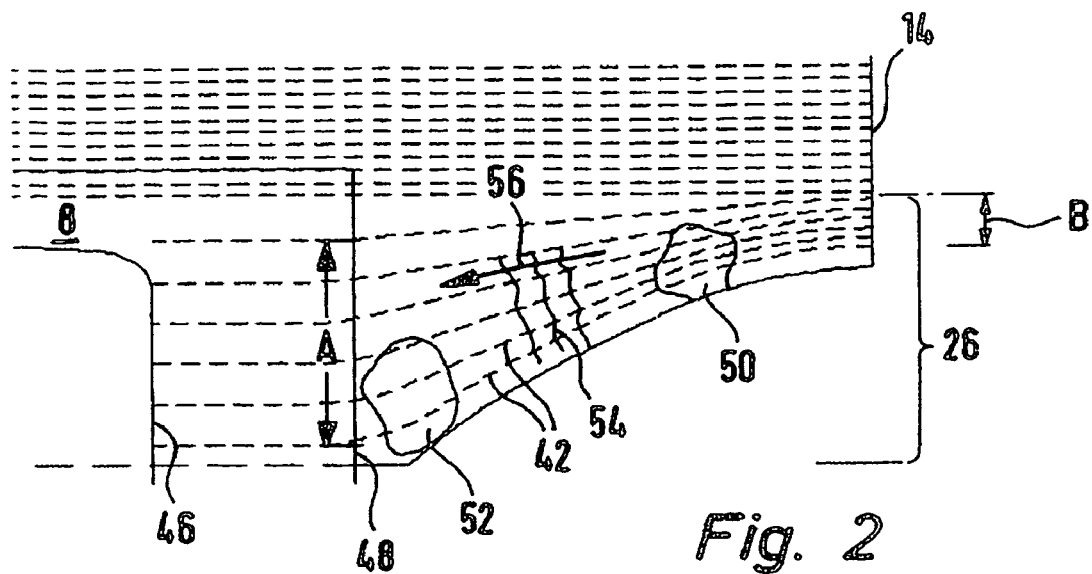
FIG. 2 shows a detail of the incontinence article of FIG. 1.
Figure 3:
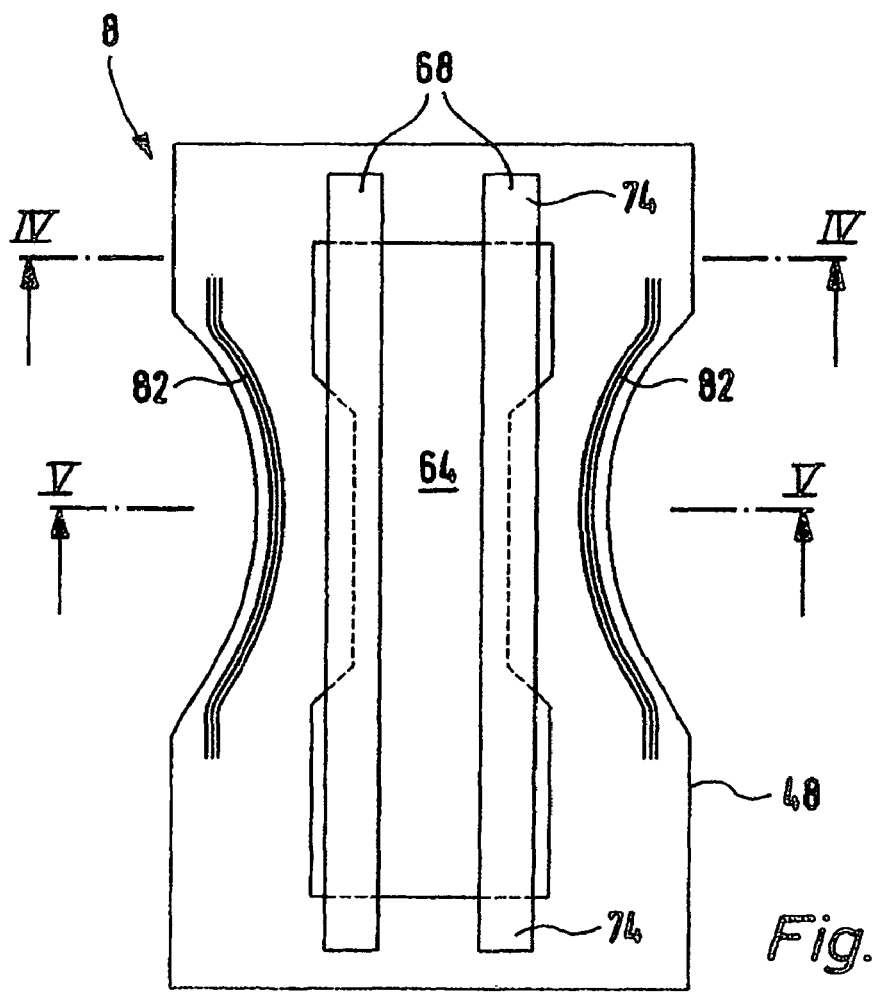
FIG. 3 shows a top view of the crotch section of the incontinence article according to FIG. 1, in turn, in the flat and extended state.

The respective area 22, 26 of the belly section 4 or the back section 6 on the crotch side facing the leg openings 19 is also elasticised. Second elastification means 40 and 42 are provided at that location. The second elastification means 40, 42 extend in each case starting from the side seam areas 14 towards a longitudinal center axis 44 of the incontinence article. As is illustrated in FIGS. 1 and 2, the second elastification means 40, 42 fan out towards the longitudinal center axis 44. This means that the separation between them increases towards the longitudinal center axis 44. This fanning out of the second elastification means 40 and 42 can also be quantitatively described in more detail with respect to FIG. 2. The second elastification means 42 (shown in FIG. 2) of the back section 6 e.g. have a minimum separation of 3 to 8 mm from each other in the side seam areas 14 (separation of directly neighboring elastification means) and a maximum separation (separation of directly neighboring elastification means) of 7 to 35 mm on an absorbent body edge 46 or longitudinal edge 48 of the crotch section 8. The fanning-out degree F. can also be defined with respect to FIG. 2:

$$F=(A-B)/B*100\%$$

This fanning-out degree may advantageously be between 50 and 900%, in particular between 100 and 700%, and moreover, in particular between 150 and 550%. It is advantageously larger in the back section 6 than in the belly section 4. The values A and B are thereby defined as the separation between the outermost second elastification means 40, 42 in the longitudinal direction 9, and the innermost second elastification means 40, 42 in the longitudinal direction 9, (i.e. not the separation between directly neighboring elastification means), i.e. A as the maximum separation, in particular, on the longitudinal edge 48 of the crotch section 8 and B as the minimum separation, in particular, in the side seam area 14.

When the fanning-out degree of the second elastification means 40, 42 is selected sufficiently large, the restoring force can be reduced within the area 22 or 26 on the crotch side facing the leg openings 19 in the direction 56 towards the crotch section 8 by ensuring that the pretension is not excessively increased due to the larger path of the second elastification means 40, 42 in consequence of the curved extension of the second elastification means 40, 42 facing away from the hip or transverse direction 16. A comparison of a region 50, which is disposed closer to the side seam area 14, of the relevant crotch-side area 22 or 26, with a region 52, which is disposed closer to the crotch section 8, shows that the restoring force that is generated when the region 52 is extensively stretched (extension in the direction of the elastification means 42) is smaller than the restoring force that is generated when the region 50 is stretched. This advantageously results in that, in consequence of the smaller elastic forces that are exerted by the second elastification means 40, 42 in the illustrated exemplary case, the chassis materials of the belly section 4 and the back section 6 are less gathered, such that the number of folds/crimps 54 is also reduced, starting from the respective side seam area 14 in the direction 56 towards the crotch section 8. Since the restoring forces that are generated through extensive stretching of the belly section in the area 22 of the belly section 4 or 26 of the back section 6 on the crotch side facing the leg openings decrease in the direction of the arrow 56, i.e. generally from the side seam area 14 towards the crotch section 8, the wear comfort is considerably improved, since, as was established in accordance with the invention, the use of elastically stretchable materials is particularly problematic especially in these areas, since these materials are particularly strained with respect to tension and extension in these areas in correspondence with the physiology of the body shape of a person. The deliberate inventive reduction of this restoring force, i.e. a reduction of the restoring force in the direction of the arrow 56, i.e. in the direction approaching the crotch section 8, provides a degree of freedom which could not be achieved before, and solves the above-mentioned problems.

Figure 8:
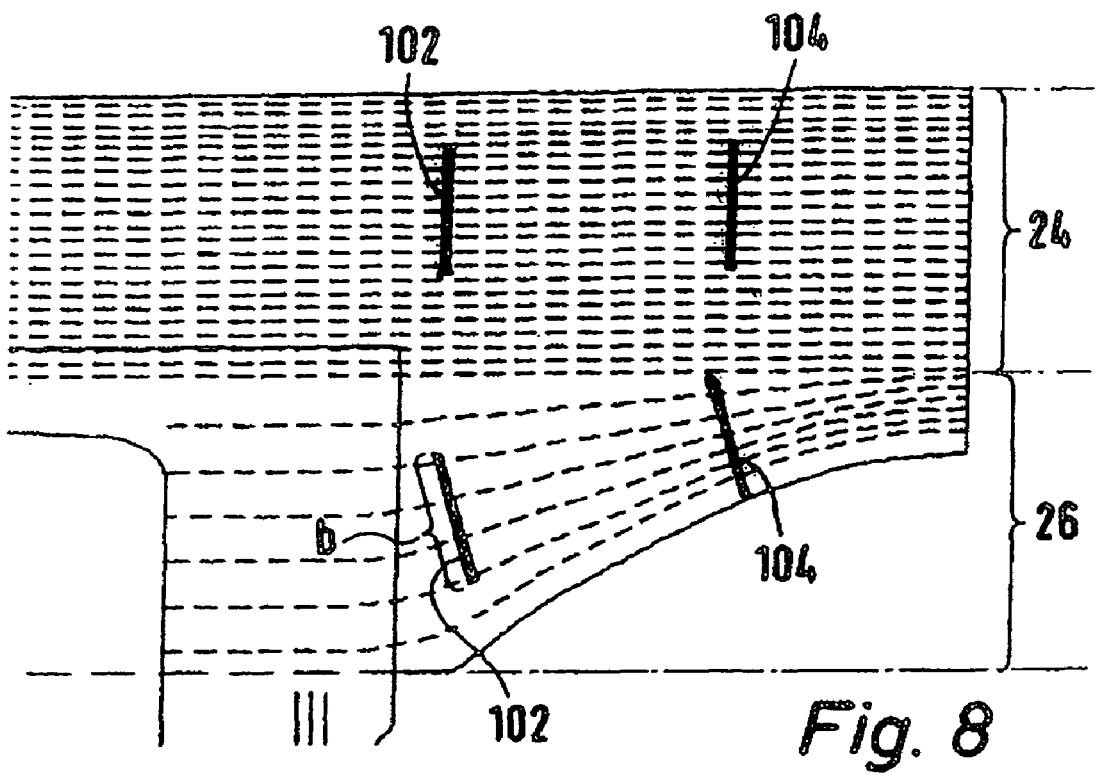
FIGS. 8, 9 clearly show as an example the determination of restoring forces in the belly section or back section of the inventive incontinence article.
Figure 9:
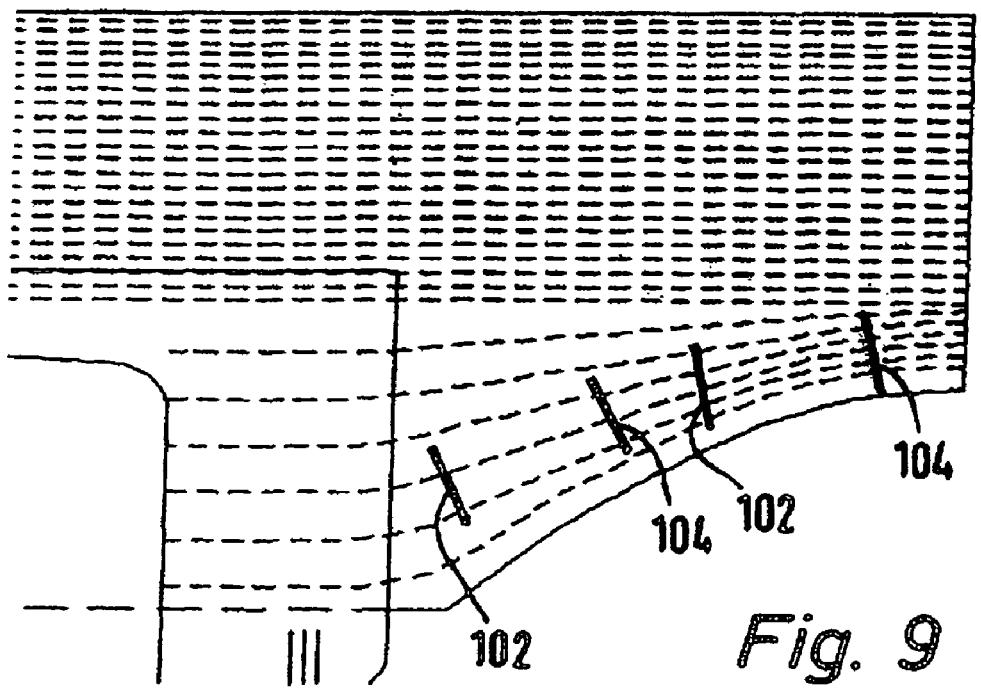

As mentioned above, restoring forces can be determined directly on the chassis of the incontinence article. Towards this end, the relevant area of the belly section 4 or of the back section 6 is clamped between two clamping jaws 102, 104 (FIG. 8) of defined identical clamping jaw width (b), and the restoring forces are then determined under defined extension of the areas to be measured of, in particular, 30% or 50% or 80% of the initial length (of the clamping jaw separation in the unclamped state) to simulate the extension exerted during use. The clamping jaws 102, 104 are thereby moved apart from each other. The clamping jaws 102, 104 should fix a maximum amount of, however at least two, neighboring elastification means 40, 42 or 28 of the area to be measured and should be substantially oriented at right angles with respect to the extension of the elastification means, such that the clamping jaws 102, 104 are extended, i.e. moved apart from each other, substantially in the direction of extension of the elastification means. This is clearly shown in FIGS. 8 and 9. FIG. 8 basically shows the arrangement of clamping jaws 102, 104 in order to compare the restoring forces in the area 22, 26 on the crotch side facing the leg openings with the restoring forces in an area 20, 24 on the hip side. FIG. 9 basically shows the arrangement of clamping jaws 102, 104 in order to compare the restoring forces in a region closer to the crotch section 8 with the restoring forces in a region closer to the side seam area 14.

In the illustrated preferred embodiment of the incontinence article 2, a separation C between the innermost second elastification means 40 of the belly section 4, facing the crotch area, and the corresponding innermost second elastification means 42 of the back section 6, facing the crotch area, is between 250 and 420 mm depending on the size of the incontinence article. The second elastification means 40, 42 substantially extend to the transverse edge 58, 60, facing the crotch area, of the belly section 4 and the back section 6. The separation between the belly section 4 and the back section 6 in the longitudinal direction 9 is 250-400 mm.

The separation between the innermost second elastification means 40, 42, facing the crotch area, and the edge contour 32, 34, defining the leg openings, of the area 22, 26 of the belly section 4 and the back section 6 on the crotch side facing the leg openings is preferably 2 to 40 mm, moreover, in particular, preferably 3 to 30 mm, in particular preferably 4 to 15 mm.

The belly section 4 and the back section 6 extend in the side seam area 14 in the longitudinal direction 9 preferably by between 100 and 220 mm. The maximum extension of the crotch section 8 in the transverse direction 16 is advantageously 200 to 350 mm.

Figure 4:
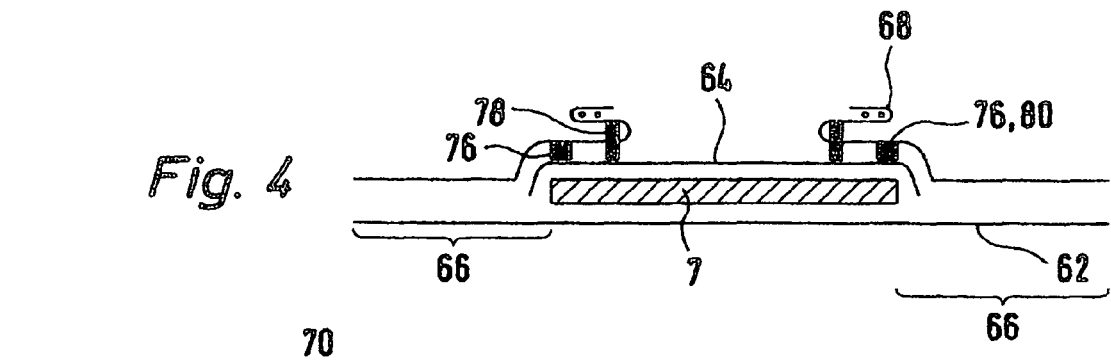
FIG. 4 shows a cross-section (schematic) along a transverse center axis of the crotch section with intersecting plane IV-IV in FIG. 3.
Figure 5:
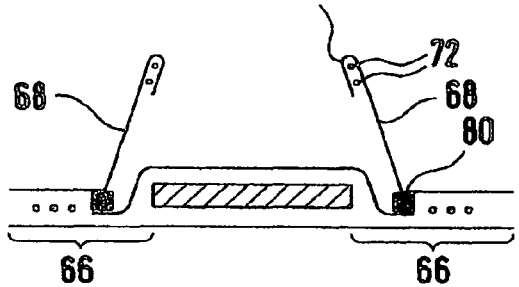
FIG. 5 shows a cross-section corresponding to FIG. 4 (schematic) of the crotch section with intersecting plane V-V of FIG. 3, with unfolded and upright barrier means.

The crotch section 8 comprises a liquid-impermeable backsheet material 62, which may be formed, in particular, by a breathable, but liquid-tight foil material, and a topsheet material 64 that is preferably based on a non-woven material. The absorbent body 7 is disposed between the backsheet material and the topsheet material (shown in FIGS. 4, 5). In the exemplary case, the backsheet material 62 forms a projection 66 that extends past the absorbent body 7 in the transverse direction 16. The topsheet 64 only slightly projects past the absorbent body 7 in the transverse direction. However, one upright barrier means 68 is provided on each side of the absorbent body 7, which extends in the longitudinal direction 9 and is typically called an upright cuff element or collar element, and is preferably formed from a hydrophobic, in particular, liquid-impermeable non-woven material, which preferably extends in the transverse direction 16 to the lateral longitudinal edges 48 of the crotch section 8. The distal ends 70 of the barrier means 68 are provided with further elastification means 72, which lift the barrier means 68 during use of the incontinence article against the skin surface of the user, as is schematically shown in FIG. 5. In their respective longitudinal end areas 74, the lateral barrier means 68 are fixed via schematically indicated fixations 76, 78 to the topsheet 64 or to themselves in a C-shaped folded configuration. It is thereby advantageous and notable that each inner fixation 78 in FIG. 4 fixes the barrier means 68 onto itself in the transverse direction 16 within the outer fixation 76, which forms a cuff base line 80 that continuously extends in the longitudinal direction 9. The inner fixation 78, however, is only provided in the longitudinal end areas 74 of the barrier means 68.

It is thereby particularly advantageous for the above-mentioned projection 66 of the backsheet material 62 and/or the topsheet material 64 which extends past the absorbent body 7 on both sides of the absorbent body, i.e. on the left-hand and right-hand side added together, to be at least 25% with respect to the largest width of the crotch section 8. This provides space in the transverse direction 16 for the arrangement of leg elastification means 82 that extend along the leg openings 19. It has turned out to be advantageous for the leg elastification means 82 to extend at a given separation from the absorbent body 7 which comprises a great deal of material and is therefore rather rigid in order not to exert any additional extension or torsional forces onto the absorbent body, which could impair its absorption properties, and also to realize a liquid-tight leg termination which is largely independent of the absorbent body. In the present case, it has turned out to be particularly advantageous for the leg elastification means 82 to terminate in the longitudinal direction 9 at a clear distance of, in particular, at least 10 mm, preferably at least 20 mm, upstream of the second elastification means 40 and 42 of the belly section 4 or the back section 6. These leg elastification means 82 preferably terminate in the longitudinal direction 9 upstream of the belly section 4 and the back section 6. This is advantageous and essential since, in this case, the leg elastification means 82 do not or hardly influence the stress behavior of the belly section 4 and the back section 6. It was found out that, in view of the inventive aim of improving the wear comfort in particular in the areas 22 and 26 of the belly section 4 and back section 6 on the crotch side facing the leg openings 19, it is disadvantageous for the leg elastification means 82, which usually have a great pretension and correspondingly large restoring forces, to additionally also extend at that location.

As is illustrated in FIG. 1, the crotch section 8 projects to relatively large extent 66 past the absorbent body 7 in the transverse direction, in particular, also in areas of the crotch section 8, which face the belly section 4 or the back section 6. This yields a relatively large overlapping area 36, 38 between the crotch section 8 and the belly section 4 and the back section 6, as mentioned above. According to a preferred embodiment variant, the overlapping area 36 of the crotch section 8 and belly section 4 covers at least 12% of the surface of the belly section 4, and the overlapping area 38 of the crotch section 8 and the back section 6 covers at least 20% of the surface of the back section 6. This is advantageous, since the crotch section 8 is thereby reliably fixed to the belly section 4 or the back section 6 even when the glue is not provided on the full surface. It is thereby also advantageously sufficient to use glue only in sections or in a pattern in order to realize a connection. This advantageously prevents the joined materials from becoming excessively rigid.

Figure 7:
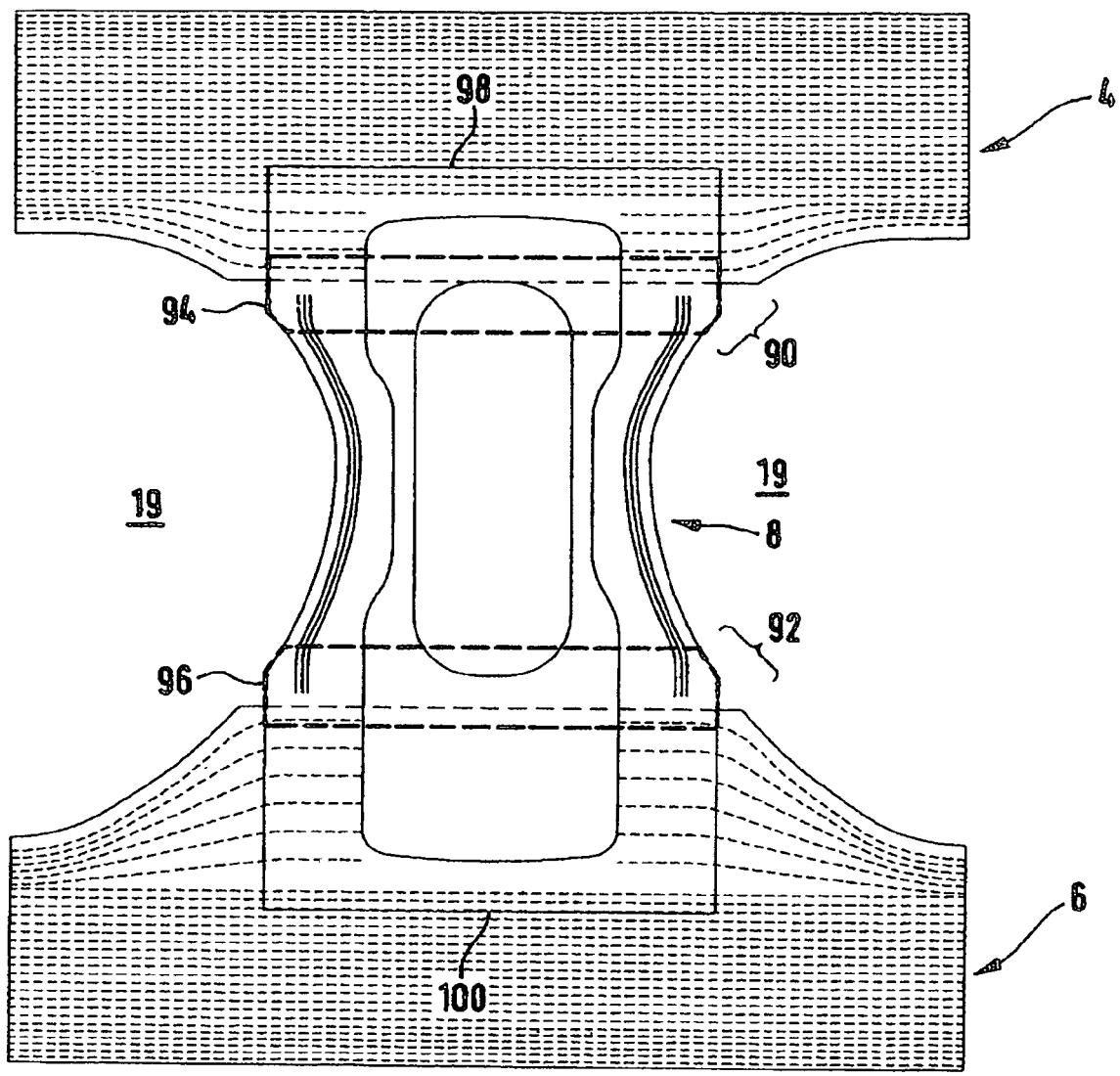
FIG. 7 shows a top view of the inventive incontinence article corresponding to FIG. 1 to clearly show the connection between the crotch section and the belly section or back section.

Another advantageous detail of the inventive incontinence article is explained with respect to FIG. 7, which corresponds to FIG. 1. The three-component concept for producing the inventive incontinence article produces a transition 90 between the crotch section 8 and the belly section 4, as well as a transition 92 between the crotch section 8 and the back section 6, which usually yields a non-continuous shape, i.e. with corners or angles or bends, of the edges of the chassis materials, which define the leg openings 19. This is dangerous in that force peaks are formed in the area of the transitions 90, 92, which could tear the chassis materials, which could, in turn, impair joining of the crotch section 8 to the belly section 4 or the back section 6. To counteract this, the liquid-impermeable backsheet material 62 of the crotch section 8 is provided with a reinforcing coating 94, 96 in the respective transition 90 and 92. It is sufficient to provide this reinforcing coating 94, 96 only in the area indicated by the dashed line of FIG. 7. In the exemplary, advantageously illustrated case, the reinforcing coating 94, 96 overlaps the belly section 4 and the back section 6 in the longitudinal direction 9 by only approximately 10 to 20 mm, in particular, by approximately 15 mm. The reinforcing coating terminates in the longitudinal direction 9 in each case upstream of the longitudinal ends 98, 100 of the crotch section, at least 30 mm upstream of the belly-side longitudinal end 98 and at least 90 mm upstream of the back-side longitudinal end 100. This is advantageous in that the reinforcing coating 94, 96 does not thereby unnecessarily reinforce the chassis materials in areas where this is not helpful but rather undesired and disadvantageous. This also saves material costs. However, the possibility to provide the reinforcing coating 94, 96 not only in the transition 90 or 92 remains unaffected.

The reinforcing coating 94, 96 advantageously consists of a non-woven material, in particular, of a spunbonded non-woven material of polypropylene, in particular, having a surface density of 10 to 20 g/m$^2$, in particular 12 to 17 g/m$^2$.

We claim:

1. An incontinence article in the form of pants for receiving body excrements, the article comprising:
    a front belly section;
    a rear back section connected to said front belly section at side seam areas on both sides during production to form a belly and back band which is continuous in a transverse or peripheral hip direction and which defines a hip opening which is closed in said peripheral hip direction;
    a crotch section permanently attached to and extending in a longitudinal direction between said belly section and said back section, said crotch section, said belly section, and said back section defining leg openings of the incontinence article, wherein said belly section and said back section have an edge contour which extends towards a transverse center axis of said crotch section and which differs from a transverse or peripheral hip direction for defining said leg openings, said crotch section further comprising a liquid-impermeable back sheet material, a top sheet material of non-woven material, and an absorbent body disposed between said top sheet and said back sheet, said back sheet material and/or said top sheet material projecting past said absorbent body in said transverse direction, wherein a maximum width of said crotch section in said transverse direction is at least 200 mm and a projection of said back sheet material and/or said top sheet material past a left-hand plus a right-hand side of said absorbent body in said transverse direction is at least 25% of a maximum width of said crotch section, wherein a surface portion of said crotch section is 25 to 55% of an overall surface of the incontinence article, wherein said crotch section overlaps at least 12% of a surface of said belly section and at least 20% of a surface of said back section;

first elastification means disposed in said belly section and said back section, said first elastification means extending at a separation from and parallel to each other in said transverse or peripheral hip direction to thereby extensively elasticize said belly section and said back section; and second elastification means disposed in an area of said belly section and said back section on a crotch side facing said leg openings, said second elastification means extending from said two side seam areas towards a longitudinal center axis of the incontinence article in a curved shape, thereby fanning out with increasing separation from each other.

2. The incontinence article of claim 1, wherein a surface portion of said crotch section with respect to an overall surface of the incontinence article is 30 to 47%, 35 to 47% or 35 to 45%.

3. The incontinence article of claim 1, wherein said projection of said backsheet material and/or said topsheet material past said absorbent body in said transverse direction on a left-hand side plus a right-hand side is at least 25%, 30 to 45% or 35 to 45% of said maximum width of said crotch section.

4. The incontinence article of claim 1, wherein said crotch section overlaps 15 to 40%, 15 to 35% or 15 to 25% of a surface of said belly section.

5. The incontinence article of claim 1, wherein said crotch section overlaps said belly section with a surface of 25,000 to 45,000 mm$^2$.

6. The incontinence article of claim 1, wherein said crotch section overlaps 20 to 40%, 20 to 35% or 22 to 32% of a surface of said back section.

7. The incontinence article of claim 1, wherein said crotch section overlaps said back section with a surface of 35,000 to 65,000 mm$^2$ or 40,000 to 55,000 mm$^2$.

8. The incontinence article of claim 1, wherein an overlap between said crotch section and said back section is larger than an overlap of said crotch section with said belly section.

9. The incontinence article of claim 1, wherein said crotch section is connected to said belly section and/or said back section in that adhesive is not applied to an entire surface.

10. The incontinence article of claim 1, wherein said absorbent body also overlaps 5 to 20% or 5 to 15% of a surface of said belly section and/or 10 to 20% or 10 to 15% of a surface of said back section.

11. The incontinence article of claim 1, wherein said belly section and said back section extend in a side seam area in said longitudinal direction by at least 100 mm, at least 150 mm or 150 mm to 220 mm.

12. The incontinence article of claim 1, wherein a minimum separation between said belly section and said back section in said longitudinal direction is 250 to 400 mm.

13. The incontinence article of claim 1, wherein a maximum extension of said crotch section in said transverse direction is 200 to 350 mm or 250 to 320 mm.

14. The incontinence article of claim 1, wherein said crotch section has leg elastification means which extend outside of said absorbent body along said leg openings and terminate in said longitudinal direction at least 10 mm or at least 20 mm upstream of said second elastification means.

15. The incontinence article of claim 14, wherein said leg elastification means terminate in said longitudinal direction upstream of said belly section and/or upstream of said back section.

16. The incontinence article of claim 14, wherein said leg elastification means extend at a variable separation from said absorbent body and have a larger separation from said absorbent body at longitudinal ends thereof than in a center.

17. The incontinence article of claim 1, wherein, in a first area of said belly section and said back section on a crotch side facing said leg openings where said second elastification means fan out, a first restoring force generated through extensive stretching of said first area is smaller than a second restoring force generated through extensive stretching of a second area on a hip side having only said first elastification means.

18. The incontinence article of claim 1, wherein, in a first area of said belly section and said back section on a crotch side facing said leg openings having said fanned-out extension of said second elastification means, a first restoring force that is generated when said first area is extensively stretched decreases in a direction towards said crotch section.

19. The incontinence article of claim 1, wherein a minimum separation between said second elastification means in said side seam areas is 3 to 8 mm, 3 to 7 mm or 3 to 6 mm.

20. The incontinence article of claim 1, wherein a maximum separation between said second elastification means on an absorbent body edge or an a longitudinal edge of said crotch section is 7 to 35 mm, 10 to 32 or 12 to 30 mm.

21. The incontinence article of claim 1, wherein said second elastification means have a fanning-out degree (F=(A−B)/3*100%) of 50 to 900%, 100 to 700% or 150 to 550%.

22. The incontinence article of claim 1, wherein a fanning-out degree (F=(A−B)/B*100%) of said second elastification means in said back section is larger than in said belly section.

23. The incontinence article of claim 1, wherein a maximum separation between said second elastification means on an absorbent body section is larger than in said belly section.

24. The incontinence article of claim 1, wherein elastic properties of said second elastification means are deactivated in an overlapping area with said absorbent body of said crotch section.

25. The incontinence article of claim 1, wherein said second elastification means have a greater pretension in correspondence with a fanned-out shape thereof than in an area where they are not fanned out.

26. The incontinence article of claim 1, wherein a separation between an innermost said second elastification means of said belly section facing said crotch area and a corresponding innermost said second elastification means of said back section facing said crotch area is 250 to 420 mm.

27. The incontinence article of claim 1, wherein a separation between innermost said second elastification means facing said crotch area and an edge contour delimiting said leg openings of said area of said belly section and said back section on said crotch side facing said leg openings is 2 to 40 mm, 3 to 30 mm or 4 to 15 mm.

* * * * *